United States Patent [19]

Hundeck et al.

[11] Patent Number: 4,774,373

[45] Date of Patent: Sep. 27, 1988

[54] PROCESS FOR MAKING 1,2-DICHLOROETHANE

[75] Inventors: Joachim Hundeck, Bonn; Harald Scholz, Erftstadt; Hans Hennen, Hürth, all of Fed. Rep. of Germany

[73] Assignee: Hoechst Aktiengesellschaft, Frankfurt am Main, Fed. Rep. of Germany

[21] Appl. No.: 554,586

[22] Filed: Nov. 23, 1983

[30] Foreign Application Priority Data

Dec. 8, 1982 [DE] Fed. Rep. of Germany ....... 3245366

[51] Int. Cl.$^4$ ............................................. C07C 17/02
[52] U.S. Cl. .................... 570/254; 570/244; 570/247
[58] Field of Search ................ 570/254, 244, 247

[56] References Cited

U.S. PATENT DOCUMENTS

| | | | |
|---|---|---|---|
| 3,222,408 | 12/1965 | Smith | 570/244 |
| 4,347,391 | 8/1982 | Campbell | 570/254 |

FOREIGN PATENT DOCUMENTS

| | | | |
|---|---|---|---|
| 3168 | 2/1966 | Japan | 570/254 |
| 819420 | 9/1959 | United Kingdom | 570/254 |
| 1186742 | 4/1970 | United Kingdom | 570/254 |

*Primary Examiner*—Howard T. Mars

[57] ABSTRACT

The disclosure relates to a process for making 1,2-dichloroethane by reacting ethylene with chlorine in a solvent in the presence of a catalyst, at a temperature of about 20° to 200° C. at atmospheric or elevated pressure, and distillatively separating the 1,2-dichloroethane from the chlorination mixture. The disclosure provides more particularly for the catalyst used to be an anhydrous tetrachloroferrate(1-) or a substance capable of forming a tetrachloroferrate(1-) in the reaction mixture.

2 Claims, No Drawings

PROCESS FOR MAKING 1,2-DICHLOROETHANE

It is known that 1,2-dichloroethane can be made by reacting ethylene with chlorine in 1,2-dichloroethane as a solvent and reaction medium. The principal by-product obtained in this reaction is 1,1,2-trichloroethane which originates from a substitution reaction dichloroethane is subjected to. In order to obviate this substitution reaction, use is made of catalysts which comprise chlorides of the elements belonging to groups IV to VI of the Periodic System, and are partially used in the presence of oxygen; more especially, anhydrous iron(III) chloride which is readily accessible and inexpensive is used.

The resulting crude catalyst-containing dichloroethane is normally taken from the reaction vessel, treated with water or an aqueous alkali metal solution so as to be freed from catalyst and hydrogen chloride contained in it, and distillatively worked up in known manner.

The use of $FeCl_3$ as a catalyst in the addition chlorination of ethylene entails certain adverse effects. In the presence of water, for example, $FeCl_3$ has corrosiveness for metallic materials such as those normally used for making reactors, columns or heat exchangers provided of course that these come into contact therewith. Needless to say, chlorine of commercial purity which is normally used for effecting the chlorination always contains traces of moisture, and hydrogen chloride originating from undesirable side reactions.

Whenever it is desirable for the heat energy set free during the chlorination of ethylene to be utilized, it is invariably necessary for the reaction to be carried out at temperatures higher than the boiling point of dichloroethane at atmospheric pressure. In view of the fact that corrosiveness increases considerably with increasing temperatures, it is indispensable to effect the chlorination reaction in apparatus lined with corrosion-resistant materials which naturally affect the commercial attractiveness of the entire process.

We have now found that anhydrous tetrachloroferrates when used as catalysts in the production of 1,2-dichloroethane are of considerably reduced corrosiveness than $FeCl_3$ for reactors which themselves are not corrosion proof. In addition to this, these compounds have been found favorably to influence by-product formation which is reduced.

The present invention relates more particularly to a process for making 1,2-dichloroethane by reacting ethylene with chlorine in a solvent in the presence of a catalyst and, if desired, an agent inhibiting by-product formation, at a temperature of about 20° to 200° C. at atmospheric or elevated pressure, and distillatively separating the 1,2-dichloroethane from the chlorination mixture, which comprises: using, as the catalyst, an anhydrous tetrachloroferrate (1-) or a substance capable of forming a tetrachloroferrate (1-) in the reaction mixture.

A preferred feature provides for the catalyst to be a tetrachloroferrate (1-) the cation of which is an alkali metal or alkaline earth metal or ammonium ion. It has also been found preferable to use the catalyst in a concentration of about 0.005 to 0.5 weight %, calculated as iron(III) chloride and based on the quantity of solvent.

A further preferred feature provides for the solvent to be 1,2-dichloroethane and for oxygen or air to be used as the inhibitor.

The following statements are intended further to illustrate the process of this invention.

The catalysts suitable for use in the process of this invention basically comprise all those tetrachloroferrates (1-) which have a solubility in the solvent, e.g. dichloromethane, sufficient for catalyzing the reaction. Use can more specifically be made of the following compounds:

| | |
|---|---|
| ammonium tetrachloroferrate (1-) | ($NH_4FeCl_4$) |
| sodium tetrachloroferrate (1-) | ($NaFeCl_4$) |
| potassium tetrachloroferrate (1-) | ($KFeCl_4$) |
| magnesium-bis[tetrachloroferrate (1-)] | ($Mg[FeCl_4]_2$) |

The catalysts can be produced in customary manner.

The catalysts can be produced in customary manner. Anhydrous ammonium tetrachloroferrate (1-) can, for example, be obtained by melting a mixture of stoichiometric proportions of ammonium chloride and anhydrous iron(III)chloride.

The catalyst should generally be dissolved or suspended in the solvent placed in a reactor. It is also possible however for the catalyst to be prepared outside the reaction solution and for it to be successively introduced into the reactor. Still further, it is possible to introduce anhydrous $FeCl_3$ and a second anhydrous component soluble in the reaction medium and capable of forming the tetrachloroferrate into the solvent initially admitted to the reactor. It is finally possible to prepare the tetrachloroferrate (1-) in the reaction mixture by introducing e.g. $(NH_4)_2FeCl_5.H_2O$ or a tetrachloroferrate (2-) into the reaction mixture, and by oxydizing this latter anion in the reaction medium to give a tetrachloroferrate (1-).

The present catalysts can be said to compare favorably with the prior art catalysts inasmuch as they are of considerably reduced corrosiveness for reactors made up of not corrosion proof metals, compared with the corrosiveness encountered in the prior art methods for making 1,2-dichloroethane. It was also found that apart from minor proportions of 1,1,2-trichloroethane (as the first substitution product) and a corresponding minor proportion of hydrogen chloride, practically no further by-products are being formed under the process conditions selected in accordance with this invention. The reaction solution remains clear even after reaction over a prolonged period provided that the solution has ammonium tetrachloroferrates (1-) contained in it. It is even possible for reaction mixture rendered dark during the reaction to re-assume a lighter coloration during the further course of the reaction, upon the addition of the compounds specified hereinabove. The present process finally ensures an almost quantitative conversion rate at high space/time-yields.

The process of this invention can be carried out, for example, in the loop reactor described in DE-OS No. 24 27 045 or any other suitable reactor.

The following Examples illustrate the invention.

EXAMPLES 1-4

About 2.0 kg 1,2-dichloroethane containing from 0.1 to 0.3 weight % of one of the dissolved catalysts specified in the Table hereinafter was introduced into a glass loop reactor which had a capacity of about 2 liters. The ascending portion of the reactor loop was provided with a layer of packing material. Disposed below the layer of packing material so as to open into the reactor were ethylene, chlorine and air inlets for the introduction of about 60 l/h each of ethylene and chlorine and 15 l/h air. The reactor liquid was circulated in the reactor system in accordance with the principle underlying a mammouth pump. During the reaction, a temperature of about 77° C. was found to establish in the reaction mixture.

Dichloroethane in vapor form which came from the reactor was condensed in a water cooler arranged above the reactor. By means of a condensate distributing means, a condensate portion corresponding to the quantity produced was taken from the cooler whilst condensate in excess was recycled to the reaction zone. By means of a cooling trap, a further dichloroethane portion was separated from issuing gas which consisted substantially of inert gases. Crude dichloroethane with the composition indicated in the Table hereinafter was obtained in an average yield of 267 g per hour. In this connection, it should be borne in mind that the gas quantities introduced were determined just by means of flow meters. Despite the fact that a steel structure was placed in the reactor, the iron content of the reaction mixture remained unchanged.

EXAMPLE 5

The procedure was as in Example 1 but 2072 g 1,2-dichloroethane containing 1.6 g dissolved $FeCl_3$ was introduced into the reactor. The solution contained 0.076 weight % $FeCl_3$, determined colorimetrically. The quantities of ethylene and chlorine introduced in the presence of air underwent reaction inside the reactor to give crude dichloroethane containing 0.18 weight % 1,1,2-trichloroethane.

Next, the reaction solution was admixed with 0.5 g $MgCl_2$. The experiment was continued over a 4 week continuous operation period and about 265 g/h crude product was obtained. Despite the fact that a steel structure was placed in the reactor, the iron content of the reaction mixture remained unchanged.

1,2-dichloroethane which was obtained in the condenser (product A) and the liquid retained in the reactor (product B) were analyzed and the following results were obtained:

|  | Product A (wgt %) | Product B (wgt %) |
| --- | --- | --- |
| $C_2H_5Cl$ | <0.002 | <0.002 |
| 1,2-EDC | 99.97 | 99.84 |
| 1,1,2-ETC | 0.021 | 0.089 |
| HCl | <0.001 | — |
| further components | 0.007 | 0.07 |

EDC = 1,2-dichloroethane
ETC = 1,1,2-trichloroethane

EXAMPLE 6

The procedure was as described in Example 5 but 2155 g 1,2-dichloroethane containing 1.7 g dissolved iron(III)chloride was introduced into the reactor. The solution contained 0.083 weight % $FeCl_3$, determined colorimetrically. The quantities of ethylene and chlorine introduced in the presence of air underwent reaction inside the reactor to give crude dichloroethane containing 0.12 weight % 1,1,2-trichloroethane.

Next, the reaction solution was admixed with 0.6 g NaCl and with additional 1,2-dichloroethane. 1,2-dichloroethane (product A) was obtained in the condenser. It was analyzed and the following results were obtained.

|  | Product A (wgt %) |
| --- | --- |
| $C_2H_5Cl$ | <0.002 |
| 1,2-EDC | 99.97 |
| 1,1,2-ETC | 0.025 |
| HCl | <0.001 |
| further components | 0.004 |

After continuous operation over a period of 10 days, a further 1.7 g $FeCl_3$ and 0.6 g NaCl were introduced into the reactor liquid so that the solution now contained 0.164 weight % iron(III)chloride. Product A obtained in the condenser was analyzed and the following results were obtained:

|  | Product A (wgt %) |
| --- | --- |
| $C_2H_5Cl$ | <0.002 |
| 1,2-EDC | 99.98 |
| 1,1,2-ETC | 0.012 |
| HCl | 0.001 |
| further components | 0.004 |

After continuous operation over a further period of 7 days, the reactor liquid was admixed once again with 1.7 g $FeCl_3$ and 0.6 g NaCl so that the solution now contained 0.248 wgt % iron(III)chloride. Product A obtained in the condenser and the reactor liquid (product B) were composed as follows:

|  | Product A (wgt %) | Product B (wgt %) |
| --- | --- | --- |
| $C_2H_5Cl$ | <0.002 | <0.002 |
| 1,2-EDC | 99.97 | 99.81 |
| 1,1,2-ETC | 0.018 | 0.068 |
| HCl | <0.001 | — |
| further components | 0.004 | 0.12 |

EXAMPLE 7

A mixture of 4341 g 1,2-dichloroethane and 3.3 g $FeCl_3$ was introduced into a stirring vessel which had a volume of 5 liters. The $FeCl_3$-content, determined colorimetrically, was 0.076 weight %. Next, 1.1 g $Na_2CO_3$ was added to the solution which was stirred magnetically. 60 l/h chlorine gas and 15 l/h air were introduced through a first inlet, and 60 l/h ethylene was introduced through a second inlet provided with a frit into the feed mixture.

Dichloroethane in vapor form which came from the reactor was condensed in a water cooler arranged above the reactor. By means of a condensate distributing means, a condensate portion corresponding to the quantity of dichloroethane produced was taken from the cooler whilst condensate in excess was recycled into the reaction zone. By means of a cooling trap, a further condensate portion was separated from the issuing gas consisting substantially of inert gases.

Product A obtained in the condenser was analyzed and the following results were obtained:

|  | Product A (wgt %) |
|---|---|
| C$_2$H$_5$Cl | <0.002 |
| 1,2-EDC | 99.96 |
| 1,1,2-ETC | 0.031 |
| HCl | 0.002 |
| further components | 0.005 |

After operation over a period of 60 hours, the solution was diluted with 1,2-dichloroethane so that its iron(III)chloride content still was 0.028 wgt %, determined colorimetrically. After operation for a further 40 hours, product A obtained in the condenser was analyzed, and the following results were obtained:

|  | Product A (wgt %) |
|---|---|
| C$_2$H$_5$Cl | <0.002 |
| 1,2-EDC | 99.96 |
| 1,1,2-ETC | 0.03 |
| HCl | 0.001 |
| further components | 0.003 |

TABLE

| Example | Catalyst | Analysis of crude product (wgt %) | | | | | |
|---|---|---|---|---|---|---|---|
|  |  | A | C$_2$H$_5$Cl | 1,2-EDC | 1,1,2-ETC | HCl | Further components |
| 1 | NH$_4$FeCl$_4$ | 0.15 | 0.004 | 99.93 | 0.06 | 0.002 | 0.003 |
| 2 | (CH$_3$)$_3$NHFeCl$_4$ | 0.13 | — | 99.86 | 0.13 | 0.01 | 0.006 |
| 3 | NaFeCl$_4$ | 0.14 | <0.002 | 99.94 | 0.03 | 0.002 | 0.005 |
| 4 | KFeCl$_4$ | 0.24 | <0.002 | 99.86 | 0.13 | 0.003 | 0.006 |

A = Concentration of catalyst, calculated as FeCl$_3$

We claim:

1. In the process for making 1,2-dichloroethane by reacting ethylene with chlorine in a solvent in the presence of a catalyst, at a temperature of about 20° to 200° C. at atmospheric or elevated pressure, and distillatively separating the 1,2-dichloroethane from the chlorination mixture, the improvement which comprises: using, as the catalyst, an anhydrous tetrachloroferrate (1-) or a substance capable of forming a tetrachloroferrate (1-) in the reaction mixture in a concentration of about 0.005 to 0.5 weight %, calculated as iron(III)chloride and based on the quantity of solvent, the cation of the tetrachloroferrate (1-) being an alkali metal or alkaline earth metal or ammonium ion.

2. The process as claimed in claim 1, wherein the solvent is 1,2-dichloroethane.

* * * * *